United States Patent [19]

McLachlan et al.

[11] Patent Number: 4,573,761
[45] Date of Patent: Mar. 4, 1986

[54] FIBER-OPTIC PROBE FOR SENSITIVE RAMAN ANALYSIS

[75] Inventors: Richard D. McLachlan; Gary L. Jewett; John C. Evans, all of Midland, Mich.

[73] Assignee: The Dow Chemical Company, Midland, Mich.

[21] Appl. No.: 531,877

[22] Filed: Sep. 14, 1983

[51] Int. Cl.[4] .............................................. G02B 5/16
[52] U.S. Cl. ............................. 350/96.24; 350/96.10; 356/301
[58] Field of Search ............... 350/96.10, 96.24, 96.25, 350/96.26, 96.29, 96.30; 356/301

[56] References Cited

U.S. PATENT DOCUMENTS

| 3,556,659 | 1/1971 | Hawes | 356/301 |
| 3,580,082 | 5/1971 | Strack | 350/96.24 X |
| 3,806,256 | 4/1974 | Ishak | 350/96.24 X |
| 3,906,241 | 9/1975 | Thompson | 356/301 X |

FOREIGN PATENT DOCUMENTS

| 112549 | 8/1980 | Japan . |
| 57-17903 | 1/1982 | Japan | 350/96.24 |

OTHER PUBLICATIONS

Cook et al, "Fiber Optic Lever Displacement Transducer," *Applied Optics*, vol. 18, No. 19, Oct. 1979, pp. 3230–3241.

McCreery, R. L.; Fleischmann, M.; Hendra, P.; "Fiber Optic Probe for Remote Raman Spectrometry," *Anal. Chem.*, Jan. 1983, 55, 146–148.

Schwab, S. D.; McCreery, R. L.; "Versatile, Efficient Raman Sampling with Fiber Optics," *Anal. Chem.*, Oct. 1984, 56, 2199–2204.

Trott, G. R.; Furtak, T. E.; "Angular Resolved Raman Scattering Using Fiber Optic Probes," *Rev. Sci. Instrum.*, Nov. 1980, 51, No. 11, pp. 1493–1496.

Hirschfeld, T. B.; "Remote Fiber Fluorimetric Analysis," *Defense Programs*, pp. 17–21, (Publication date unclear).

Primary Examiner—John Lee

[57] ABSTRACT

A fiber-optic probe, useful for light scattering and luminescence measurements, which comprises at least one optical fiber for transmitting light into a sample and at least two optical fibers for collecting light from the sample. The probe may further comprise a shield surrounding the fibers and having an optical window at one end to protect the fibers from hostile environments. When used in conjunction with a laser as a light source, the probe is particularly suited for Raman spectroscopy.

14 Claims, 2 Drawing Figures

FIBER-OPTIC PROBE FOR SENSITIVE RAMAN ANALYSIS

The subject of this invention is a fiber-optic probe useful for both light scattering and luminescence measurements. In particular, the probe is useful for Raman spectroscopy.

BACKGROUND OF THE INVENTION

The use of light for measuring certain physical and chemical characteristics has been known in laboratories for some years. For example, both qualitative and quantitative analyses are frequently made using spectroscopic techniques. The advent of both lasers and optical fibers have greatly increased the activity in this field. In particular, optical fibers have allowed the locating of sensitive and expensive equipment remote from harsh reactor environments, thus making light analysis techniques suitable for application to commercial processes.

One analytical technique that could be useful for commercial applications is Raman spectroscopy. When light of a single wavelength interacts with a molecule, the light scattered by the molecule contains small amounts of light with wavelengths different from that of the incident light. This is known as the Raman effect. The wavelengths present in the scattered light are characteristic of the structure of the molecule, and the intensity of this light is dependent on the concentration of these molecules. Thus, the identities and concentrations of various molecules in a substance can be determined by illuminating the substance with light of a single wavelength and then measuring the individual wavelengths, and their intensities, in the scattered light. The details of Raman spectroscopy are discussed in U.S. Pat. No. 3,556,659 wherein further references are also cited for the theory of the Raman effect.

A major difficulty associated with Raman spectroscopy is the low intensity of the scattered light compared to the exciting light. Elaborate spectrometers, having high light gathering power and dispersion, high stray light rejection, and sensitive detectors, are required to isolate and measure the low intensity Raman scattered light. These instruments are costly and sensitive, and thus are not well suited for use in commercial manufacturing or processing facilities. As a result, they have rarely been used outside of laboratory environments. A simplified fiber-optic probe that could be located at a point remote from its light source and from its spectrometer could make Raman spectroscopy available for analyzing commercial processes.

For light measurements, a sensing probe is normally designed to maximize the overlap between the are illuminated by a fiber transmitting light into a sample and the area viewed by a fiber collecting light from the sample. Ideally, then, a single fiber should be used for both transmitting and collecting light as discussed by Hirschfeld in his article "Remote Fiber Fluorimetric Analysis," *Defense Programs*, p. 17. This is not feasible, however, in Raman spectroscopy due to the low intensity of the Raman scattered light. The light being transmitted down the fiber excites the molecules of the fiber itself and thus generates Raman scattering within the fiber which interferes with Raman scattered light collected by the fiber from the sample. A multifiber probe, therefore, with the fibers performing independent functions of transmitting and collecting, must be used.

A probe having two fibers is described in Japanese Pat. No. 55-112549. That reference, however, teaches that lenses are necessary at the fiber ends for focusing the laser (exciting) light and for collecting the Raman (scattered) light. The proper alignment of these focusing lenses is necessarily critical to achieve a common image point, but such alignment is difficult to achieve due to the very small diameters (typically less than 1000 microns) of the fibers. The focusing lenses thus greatly add to the cost and complexity of the probe and thereby render it less attractive for commercial processes.

The present invention offers a significant improvement in that it describes a relatively simple probe, useful for Raman analysis, that can be easily modified for many diverse applications.

SUMMARY OF THE INVENTION

The probe of this invention comprises optical fibers grouped in a bundle wherein at least one optical fiber is used exclusively for transmitting light into the sample while at least two optical fibers arranged at an advantageous angle with the transmitting fiber are used exclusively for collecting light from the sample. The probe may also include a shield surrounding the bundle to protect it from any hostile environment in which it is inserted.

By starting that the optical fibers are grouped in a "bundle," it is contemplated that the fibers should be in a closely packed arrangement with the fiber axes approximately parallel and with minimum spacing between the fiber ends. This means that the fiber ends preferably should be touching each other.

The terms "optical fiber" and "fiber-optic" are used herein interchangeably to refer to fibers capable of transmitting light. The term "fiber" is intended to include both single- and multi-filament fiber-optics.

DETAILED DESCRIPTION OF THE INVENTION

Figure 1:
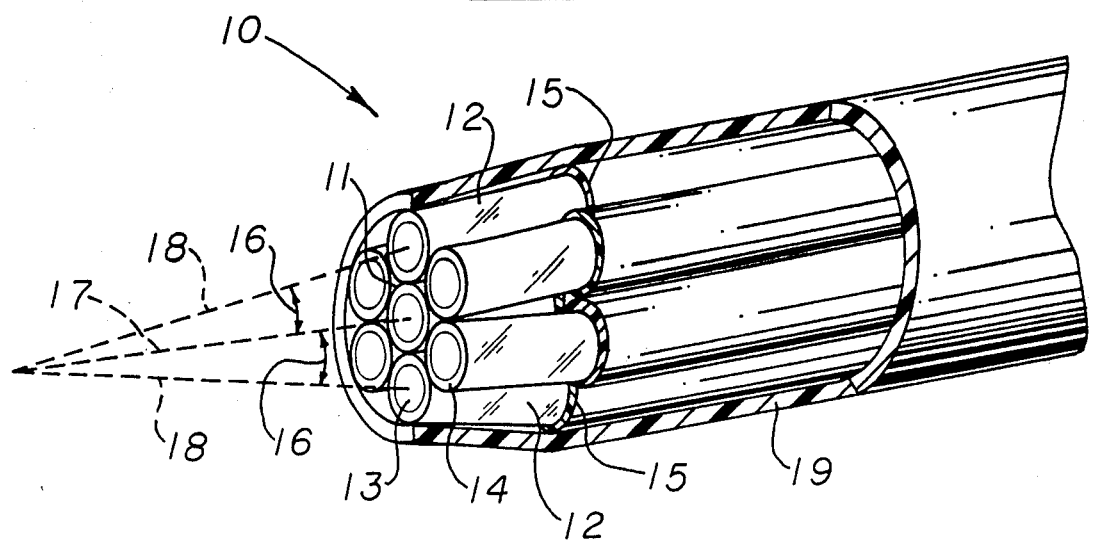
FIG. 1 is an isometric view, partly in section, of a preferred embodiment of the arrangement of fibers within the probe.

A single optical fiber for transmitting light into the sample is adequate for typical applications. To maximize the overlap between the area illuminated by that single fiber and the area viewed by all of the collecting fibers, it is preferable that the single transmitting fiber be located in the center of the fiber bundle. The collecting fibers can then be located around the circumference of the transmitting fiber. FIG. 1 shows probe 10 having a transmitting fiber 11 surrounded by six collecting fibers 12.

The strength of the Raman signal that can be generated using the probe of this invention decreases dramatically as the separation between the individual fibers are increased within the probe itself. It is preferable, then, to minimize the spacing between the fibers within the bundle. It is most preferable that the ends of the fibers be in direct (touching) contact with each other. To achieve this minimum spacing in the configuration described above, wherein there is a single central transmitting fiber surrounded by a number of collecting fibers, it is necessary that the transmitting fiber diameter be no greater than the diameter of the collecting fibers.

The greater the number of collecting fibers in the probe, the greater the amount of Raman scattered light that can be collected and therefore the greater the Raman signal that will be generated. Two collecting fibers work well in the present probe, but preferably there should be from 3 to 7 collecting fibers around the transmitting fiber. The highly preferred configuration of FIG. 1 is a seven fiber probe 10 having one central transmitting fiber 11 surrounded by six collecting fibers 12.

The fibers of the present probe are preferably single filament fibers. Each fiber has a transparent core 13, commonly of glass of fused silica, enclosed in a transparent cladding 14 having a lower refractive index than the core. Each fiber is shielded by an opaque jacket 15. These fibers are available commercially with core sizes ranging from about 50 microns in diameter to about 1,000 microns in diameter. For efficient collection of Raman scattered light, and for ease of construction of the probe, it is preferable to use optical fibers having core diameters ranging from about 200 microns to about 700 microns. Within this range, optical fibers having core diameters of about 600 microns are most preferred.

Besides minimizing the spacing between the fibers in the bundle, changing the angle 16 formed between the axis 17 through the end of the transmitting fiber and the axes 18 through the ends of the collecting fibers has been found to improve the performance of the probe. If the ends of the collecting fibers are tilted slightly toward the center of the probe so that the axes of the collecting fibers and the axis of the transmitting fiber converge slightly at the fiber ends, then the performance of the probe will improve. This improvement in performance increases as the angle of convergence increases from zero to an angle between about 10 degrees and about 200 degrees. As the angle of convergence increases beyond that range, the performance decreases such that the performance at an angle of convergence of about 45 degrees is approximately the same as that when the fibers are parallel (zero degree angle of convergence).

The desired angle of convergence is achieved during construction of the probe by removing the protective jackets 15 from the fibers for some distance, say 5 millimeters, from the ends of the fibers so that upon pinching the fiber ends together (to minimize the spacing) the desired angle will result. The fibers are retained in the proper positions by confining the fibers in heat shrink tubing 19. The angles of convergence of the fibers can be controlled alternatively by adding small shims between the fibers at a distance from the end of the fiber bundle.

This invention contemplates an optical fiber probe that may be used for many diverse industrial applications. In these applications the probe may be subjected to varying environments, some of which can be hostile to the fibers themselves. Under these circumstances, the fiber bundle should be protected from the environment by enclosure in a protective shell. The design of such a shell, including the shell material, will depend on the particular application. The shell should be adapted for insertion in, and connection to, a process vessel such as a reactor.

Figure 2:
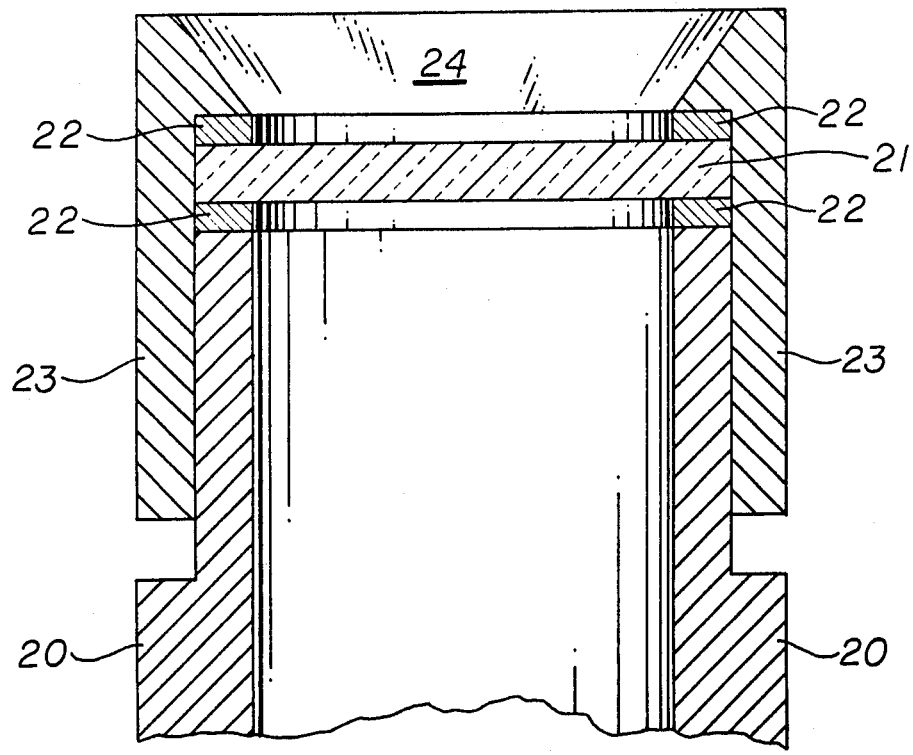
FIG. 2 is a side elevation view in cross-section of an embodiment of the protective shell for the probe.

FIG. 2 shows one example of an appropriate shell design. A tube 20 encases the fiber bundle (not shown) with a window 21 across the tube end adjacent to the ends of the fibers. The window must have sufficient optical clarity so that it does not interfere with, or alter, the transmittance of light to or from the fiber ends. Suitable materials for the window are, for example, fused silica or crystals of sapphire and diamond.

The window 21 is sealed across the end of the tube 20 with gaskets 22 located in the shell cap 23 which forms a press (or interference) fit with the tube. Other means for sealing the cap onto the tube, such as a threaded fitting, are also suitable. The cap is shown as having a convex opening 24 away from the window so as to not impinge on the areas illuminated and viewed by the fibers.

The materials used for the components of the protective shell should withstand the environment to which the probe is subjected. For many applications, Monel steel is a suitable material for the shell tube 20 and for the shell cap 23, and nickel is a suitable material for the gaskets 22.

Another type of protective shell that has proved useful is one made entirely from glass with the end adjacent to the bundle end being optically ground. The need for a separate window and for sealing gaskets is thereby eliminated.

Operation

When the fiber-optic probe of the present invention is used for Raman spectroscopy, light generated by a laser should be used as the excitation light. A suitable light source is an argon ion laser.

At a remote distance from the probe, the central transmitting fiber is isolated from the other fibers of the bundle and optically connected, by using means well known in the art, to a laser. The remaining ends of the collecting fibers emerging from the probe are adapted for connection to a Raman spectrometer. For such a connection, the fiber ends preferably are arranged linearly.

Once the proper connections have been made to the laser and to the Raman spectrometer, the probe is inserted into the medium to be analyzed. The laser light is then directed into the transmitting fiber which transmits the light into the medium. The collecting fibers collect light scattered within the medium and transmit that light back to the spectrometer for analysis.

The optical fiber probe of this invention is also useful for other light scattering or luminescence measurements, such as fluorescence. In such applications, it may be possible to use light sources other than lasers, including light emitting diodes. The present invention contemplates all such uses of this optical fiber probe.

What is claimed is:

1. A fiber-optic probe for sensitive Raman analysis and useful for light scattering or luminescence measurements, generally, the probe beneficially not requiring a focusing lens and comprising:

(a) at least one optical fiber for transmitting light into a sample; and (b) at least two optical fibers for collecting light from the sample which are in closely spaced relationship with the transmitting fiber for purposes of sensitive Raman analysis; wherein the collecting fibers converge with the axis of the transmitting fiber at an angle less than 45 degrees and which produces substantially greater sensitivity for Raman analysis than if arranged parallel.

2. The probe of claim 1 wherein the fiber ends are grouped in a bundle and the transmitting fiber is arranged centrally in the bundle.

3. The probe of claim 1 wherein there is minimum spacing between the fibers.

4. The probe of claim 1 wherein the fibers are single filament fibers.

5. The probe of claim 1 wherein the core diameter of the transmitting fiber is no greater than the core diameter of the collecting fibers.

6. The probe of claim 1 wherein the angle of convergence is generally from about 10 degrees to about 20 degrees.

7. The probe of claim 1 wherein there is one transmitting fiber and from about 3 to about 7 collecting fibers.

8. The probe of claim 7 wherein the angle of convergence is generally from about 10 degrees to about 20 degrees.

9. The probe of claim 8 wherein there are six collecting fibers arranged in close spacing about the circumference of the transmitting fiber.

10. The probe of claim 1 wherein the fiber core diameters are from about 200 microns to about 700 microns.

11. The probe of claim 10 wherein all of the fiber core diameters are generally about 600 microns.

12. The probe of claim 11 wherein the angle of convergence from about 10 degrees to about 20 degrees.

13. The probe of claim 12 wherein there is from 3 to about 7 collecting fibers arranged about a transmitting fiber.

14. A method for Raman spectroscopic analysis utilizing the probe of claim 1 wherein laser light is directed into the transmitting fiber and transmitted to the sample and light scattered within the sample is collected and transmitted to a spectrometer by the collecting fibers.

* * * * *